United States Patent [19]

Yen et al.

[11] 4,219,411
[45] Aug. 26, 1980

[54] CELL SORTING APPARATUS

[75] Inventors: Shiao-Ping S. Yen; Alan Rembaum, both of Altadena, Calif.; Robert S. Molday, Vancouver, Canada

[73] Assignee: California Institute of Technology, Pasadena, Calif.

[21] Appl. No.: 943,453

[22] Filed: Sep. 18, 1978

Related U.S. Application Data

[63] Continuation of Ser. No. 789,268, Apr. 20, 1977, Pat. No. 4,157,223, which is a continuation-in-part of Ser. No. 694,151, Jun. 9, 1976, abandoned.

[51] Int. Cl.$^2$ .............................................. B03C 1/14
[52] U.S. Cl. ........................................ 209/213; 209/8; 209/39; 209/223 R
[58] Field of Search ............... 209/213, 214, 215, 227, 209/223 R, 232, 39

[56] References Cited

U.S. PATENT DOCUMENTS

| | | | |
|---|---|---|---|
| 360,842 | 4/1887 | Atkins | 209/215 X |
| 1,474,624 | 11/1923 | Davis | 209/215 |
| 2,642,514 | 6/1953 | Herkenhoff | 209/215 X |
| 2,714,960 | 8/1955 | Schmid | 209/227 |
| 3,289,836 | 12/1966 | Weston | 209/227 X |
| 3,294,237 | 12/1966 | Weston | 209/227 X |
| 3,607,718 | 9/1971 | Aubrey | 209/223 R |
| 3,627,678 | 12/1971 | Marston | 209/214 X |
| 3,902,994 | 9/1975 | Maxwell | 209/232 X |
| 4,102,780 | 7/1978 | Sun | 209/39 |

FOREIGN PATENT DOCUMENTS 464514  7/1975  U.S.S.R. ................................. 209/215

Primary Examiner—Robert Halper
Attorney, Agent, or Firm—Poms, Smith, Lande & Rose

[57] ABSTRACT

Polymeric functional microspheres containing metal or metal compounds are formed by addition polymerization of a covalently bondable olefinic monomer such as hydroxyethylmethacrylate in the presence of finely divided metal or metal oxide particles, such as iron, gold, platinum or magnetite, which are embedded in the resulting microspheres. The microspheres can be covalently bonded to chemotherapeutic agents, antibodies, or other proteins providing a means for labeling or separating labeled cells. Labeled cells or microspheres can be concentrated at a specific body location such as in the vicinity of a malignant tumor by applying a magnetic field to the location and then introducing the magnetically attractable microspheres or cells into the circulatory system of the subject. Labeled cells can be separated from a cell mixture by applying a predetermined magnetic field to a tube in which the mixture is flowing. After collection of the labeled cells, the magnetic field is discontinued and the labeled sub-cell population recovered.

8 Claims, 3 Drawing Figures

CELL SORTING APPARATUS

ORIGIN OF THE INVENTION

The invention described herein was made in the performance of work under a NASA contract and is subject to the provisions of Section 305 of the National Aeronautics and Space Act of 1958, Public Law 83-568 (72 Stat. 435; 42 USC 2457).

CROSS-REFERENCE TO RELATED APPLICATION

This is a continuation of application Ser. No. 789,268, filed Apr. 20, 1977, now U.S. Pat. No. 4,157,223, which in turn is a continuation-in-part of Ser. No. 694,151, filed June 9, 1976, now abandoned.

BACKGROUND OF THE INVENTION

1. Field of the Invention

The present invention relates to small, polymeric, functional microspheres, to methods of making the microspheres and to their use in labeling and separating biological cells.

2. Description of the Prior Art

The isolation and characterization of cell membrane and their components is essential for an understanding of the role in which surface membranes play in regulating a wide variety of biological and immunological activities. The present techniques used for this purpose are not quite satisfactory.

Knowledge of the nature, number and distribution of specific receptors on cell surfaces is of central importance for an understanding of the molecular basis underlying such biological phenomena as cell-cell recognition in development, cell communication and regulation by hormones and chemical transmitters, and differences in normal and tumor cell surfaces. In previous studies, the localization of antigens and carbohydrate residues on the surface of cells, notably red blood cells and lymphocytes, has been determined by bonding antibodies or lectins to such macromolecules as ferritin, hemocyanin or peroxidase which have served as markers for transmission electron microscopy. With advances in high resolution scanning electron microscopy (SEM), however, the topographical distribution of molecular receptors on the surfaces of cell and tissue specimens can be readily determined by similar histochemical techniques using newly developed markers resolvable by SEM.

Recently commercially available polystyrene latex particles have been utilized as immunologic markers for use in the SEM technique. The surface of such polystyrene particles is hydrophobic and hence certain types of macromolecules such as antibodies are absorbed on the surface under carefully controlled conditions. However, such particles stick non-specifically to many surfaces and molecules and this seriously limits their broad application.

The preparation of small, stable spherical particles which are bio-compatible, i.e., do not interact non-specifically with cells or other biological components and which contain functional groups to which specific proteins and other biochemical molecules can be covalently bonded is disclosed in copending application Ser. No. 434,124, filed January 17, 1974, now issued on May 18, 1976 as U.S. Pat. No. 3,957,741.

Smaller, more evenly shaped microspheres are disclosed in Ser. No. 634,935, filed Nov. 24, 1975 and microspheres having a density differing from that of cell membranes are disclosed in Ser. No. 634,429, filed Nov. 24, 1975, now issued on July 12, 1977 as U.S. Pat. No. 4,035,316.

The hydroxyl groups can be activated by cyanogen bromide for covalent bonding of proteins and other chemicals containing amino groups to the polymeric latex. Methacrylic acid residues which impart a negative charge onto the particles are likely to prevent non-specific binding to cell surfaces and to provide carboxyl groups to which a variety of bio-chemical molecules can be covalently bonded using the carbodiimide method. Cross-linking of the polymeric matrix is preferable in order to maintain the stability and size of the particles in both aqueous solution and in organic solvents commonly used in the fixation and dehydration of biological specimens for electron or light microscopy.

These polymeric microspheres ranging in diameter from 300 Å to 2000 Å have been successfully utilized as biocompatible immunochemical markers of red cells and lymphocytes in scanning electron and light microscopy. The variable density microspheres have been utilized in separation of labeled cells to which they are attached.

Introduction of small amounts of finely divided metals into polymeric functional microspheres would eliminate the necessity to bind radioactive or fluorescent tags to the microspheres. The metal containing micropheres can be readily detected by x-ray electron probe methods since the presence of metal causes the microspheres to be electron dense.

SUMMARY OF THE INVENTION

Polymeric microspheres capable of specific covalent binding to proteins and of improved separation of living cells such as cellular elements of peripheral blood or membrane receptor sites from cellular organelles are provided by this invention. The microspheres are synthesized by, in situ, incorporating into the functional polymeric microspheres an effective amount of finely-divided metal or metal compound particles. The metal containing microspheres can readily be detected by x-ray microscopy. The in situ polymerization technique results in a uniform dispersion of the particles throughout the microspheres. It is believed that the metal oxide particles such as $Fe_3O_4$ in the presence of water and Co gamma irradiation exhibit a redox catalytic activity. The particles thus act as active catalyst centers for initiation of the polymeric addition reaction causing both promotion of the reaction and contributing to a more uniform presence of metal material in the microspheres produced.

The microspheres are produced by addition polymerization of a liquid polymerization system including a dispersion of the metal particles in a monomer mixture containing a covalently bondable unsaturated monomer. Free radicals may be generated by free radical catalysts or by high energy radiation. More uniformly sized and shaped beads are formed in very dilute aqueous monomer mixtures. Surfactants may be present to aid in the dispersion of the metal particles and in suspending the microspheres.

Separation of magnetic or magnetically attractable microsphere labeled cells is effected by applying a magnetic field to the mixture of labeled and unlabeled cells and collecting the labeled cells at the location of highest field flux. Improved rate of specific cell binding is practiced by applying magnetic field at a body location such as at a tumor while injecting antigen or antibody labeled magnetic microspheres into the stream of the subject. The magnetically attractable microspheres will accumulate and remain within the field and probability of specific cell reaction is increased. This technique could also be utilized as a chemotherapeutic delivery system by covalently binding a chemotherapeutic agent to the microsphere.

The microsphere can be utilized to yield a biochemical mapping of the membrane with respect to assessment of surface receptors which can redistribute in the plane of the membrane in response to a matrix containing rigidly displayed ligands. This will be useful in determining the contributing roles of the restriction of movement of certain surface receptors to oncogenic transformation of cells. Other applications include the isolation of differentiated regions of cell surface membranes, and studies of this nature would be of great utility in areas such as developmental biology.

The microspherical beads containing hydroxyl or amine groups covalently bond to antibodies and other biological materials and are useful as specific cell surface markers for scanning electron microscopy. The particles are found to bind to hormones, toxins, lectins, antibodies, sugars and other molecules and have application in the detection and localization of a variety of cell surface receptors. Particles tagged with fluorescent dye or radioactive molecules serve as sensitive markers for fluorescent microscopy and as reagents for quantitative study of cell surface components. By covalently bonding lectins, antigens, hormones and other molecules to these spheres, detection and localization of specific carbohydrate residues, antibodies, hormone receptors and other specific cell surface components or fragments can also be isolated and determined. These reagents also have application in highly sensitive radioimmune assays, as visual markers for fluorescent and transmission electron microscopy, for radioactive quantitation of specific cell surface receptors and as potential therapeutic reagents.

The microspheres are hydrophilic, hydrolytically stable, biocompatible and have good mechanical strength. The microspheres are of well characterized structure, of outstanding purity and the hydrophilic properties, size, and mechanical properties can be systematically varied by selection of monomers and polymerization conditions.

These and many other features and attendant advantages of the invention will become apparent as the invention becomes better understood by reference to the following detailed description when considered in connection with the accompanying drawings.

DESCRIPTION OF THE PREFERRED EMBODIMENTS

Figure 1:
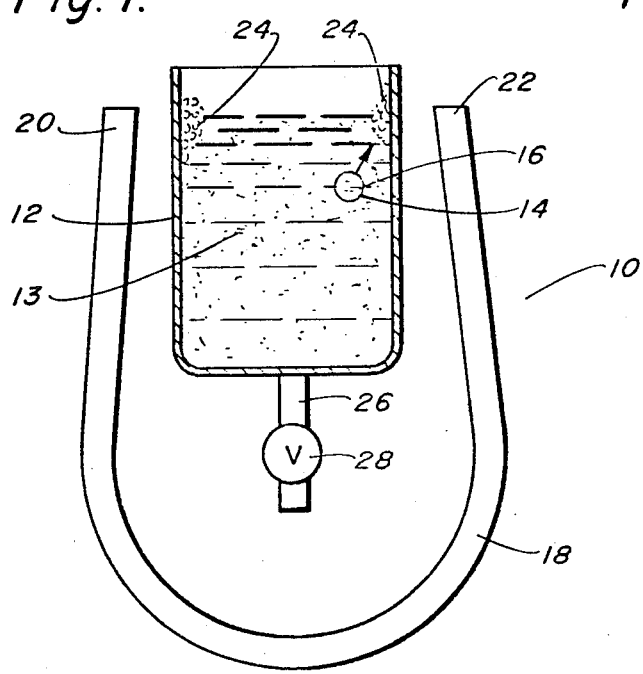
FIG. 1 is a schematic view of a static-mode magnetic cell separator.

The microspheres are preferably produced by aqueous suspension addition polymerization of a monomer mixture including at least 20%, by weight, of an olefinically unsaturated monomer containing a covalent bonding group such as hydroxyl, carboxyl or amino. Polymerization may be initiated by means of a free radical catalyst such as 0.003 to 0.1 percent by weight of a persulfate such as ammonium persulfate or a peroxide, hydroperoxide or percarbonate.

Polymerization can proceed by heat alone in absence of free radical catalyst at temperatures above 50° C. However, it is preferred to conduit the addition polymerization at lower temperature by means of high energy radiation. The polymerization proceeds with or without stirring with application of high energy radiation capable of generating free radicals in the aqueous system. The radiation source is suitably a cobalt 60 gamma source or cesium source and doses of 0.5 to 1.0 megarads are sufficient for polymerization. It is believed that polymer chains grow from the surface of metallic particles. The reaction is preferably conducted under oxygen excluding condition, generally by applying vacuum to the reaction vessel or by displacing oxygen gas from the system with an inert gas such as nitrogen. After polymerization has proceeded to completion, the reaction mixture is made neutral by adding acid or base, passed through mixed ion exchange resins to remove emulsifiers or any free metal particles. Further purification is achieved by centrifugation on a sucrose gradient.

The addition of 0.05 to 5%, by weight, of a stabilizing agent to the aqueous polymerization system before polymerization is found to further reduce agglomeration. The stabilizing agent is suitably an aqueous soluble polymer such as a polyalkylene oxide polyether or nonionic surfactants such as Tween which are polyoxyethylene derivatives of fatty acid partial esters of sorbitol, Triton X, or dextranes. The polyethers generally have a molecular weight from 10,000 to 10,000,000, preferably 400,000 to 6,000,000 and are polymers of ethylene oxide, propylene oxide or their mixtures. Polyethylene oxides (PEO) and Triton X are preferred.

The uniformly small sized microspheres can also be synthesized by the substantially instantaneous free radical initiated aqueous emulsion polymerization containing a very dilute total monomer content, suitably from 0.5 to 35% and preferably from 3% to about 20% by weight. The microspheres are hydrophilic, hydrolytically stable, are biocompatible and of sufficient mechanical strength by weight.

The composition of the monomer mixture is essential to obtain beads of the desired characteristics. The monomers should be substantially water-soluble under the conditions of polymerization such that oil droplets do not form as in conventional emulsion polymerization in order to form the extremely fine, (less than 300 Å) uniformly-shaped beads.

The amount of free radical catalyst also influences the size of the beads for a given monomer concentration. As the amount of catalyst is increased the size of the beads decreases. However, the reaction at increased catalyst level becomes too fast to control causing uneven size distribution. The free radical catalyst is usually present in an amount from 0.003 to 0.1 percent by weight of the polymerization mixture. Representative free radical catalytic initiators are ammonium persulfate (AP); or other inorganic persulfate, benzoyl peroxide, t-butyl peroctoate, isopropyl percarbonate, cumene hydroperoxide, dicumyl peroxide, 1,3-bis(t-butylperoxyisopropyl)-benzene, methyl ethyl ketone peroxide, acetyl peroxide, di-t-butylperoxide, t-butyl hydroperoxide, azo compounds such as azodiisobutyronitrile and the like.

Also present in the polymerization mixture is a surface active agent such as sodium dodecyl sulfate (SDS), octylphenocypolyethoxy ethanol, sodium lauryl sulfate, sodium stearate and others. Increasing levels of surface active agent results in smaller bead diameter. However, for biological analytical uses, the surfactant must be removed from the final bead suspension. Therefore, low levels in the range of 0.03 to 0.5 parts by weight of the polymerization mixture are preferred.

The monomers are freshly vacuum distilled before polymerization to remove impurities and inhibitor, if present. The polymerization reaction is preferably conducted in the absence of oxygen, suitably in vacuum or in the presence of an inert gas such as argon. In order to assure uniformity of particle size and to foster uniform initiation throughout the polymerization mixture, the polymerization mixture is intimately stirred before initiation, for example, by tumbling the polymerization container for about 5 minutes before subjecting the mixture to heat.

Initiation is defined as the step of creating a free radical followed by addition of the free radical to an unsaturated bond of the monomer. In the present process, initiation should occur throughout the volume of the polymerization mixture within 10 to 60 seconds or applying heat to the mixture. In the particular embodiment the container is placed in a bath and hot water was added to the bath. The container is then immersed in the hot water and rotated for polymerization.

The temperature of the bath must be at or above the decomposition temperature of the free radical catalyst and suitably at a higher temperature. For example, in the case of ammonium persulfate, initiation at 60° C. will be slow resulting in nonuniformly sized beads having diameters larger than desired. However initiation at 100° C. results in initiation and propagation at nearly quantitative yield of very small, uniformly-shaped particles within about one hour and the size distribution is within ±10% of the average size. Mixing such as by tumbling should continue throughout the polymerization step.

Mono-unsaturated covalent, bonding monomers are freely water soluble and should comprise from 25–95% of the monomer mixture. These monomers are suitable selected from amino, carboxyl or hydroxyl substituted acrylic monomers. Exemplary monomers are acrylamide (AM), methacrylamide (MAM), acrylic acid, methacrylic acid (MA), dimethylaminomethacrylate or hydroxyl-lower alkyl- or amino-lower-alkyl-acrylates such as those of the formula:

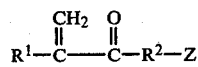

where $R^1$ is hydrogen or lower alkyl of 1–8 carbon atoms, $R^2$ is alkylene of 1–12 carbon atoms, and Z is —OH or $R^3$—N—$R^4$ where $R^3$ or $R^4$ are individually selected from H, lower alkyl, or lower alkoxy of 1–8 carbon atoms. 2-hydroxyethyl methacrylate (HEMA), 3-hydroxypropyl methacrylate and 2-aminoethyl methacrylate are readily available commercially. Porosity and hydrophilicity increase with increasing concentration of monomer.

Inclusion of polyunsaturated compounds also provides cross-linked beads which are less likely to agglomerate. The polyunsaturated compounds are generally present in the monomer mixture in an amount from 0.1–20% by weight, generally 6–12% by weight and are suitably a compatible diene or triene polyvinyl compound capable of addition polymerization with the covalent bonding monomer such as ethylene glycol dimethacrylate, trimethylol-propane-trimethacrylate, N,N'-methylene-bis-acrylamide (BAM) hexahydro-1,3,5-triacryloyl-s-triazine or divinyl benzene.

For small particle size the monomer mixture preferably contains a large percentage, suitable from 40–70% of sparingly water soluble monomers having hydrophobic characteristics since this is found to result in freely suspended individual small beads. In the absence of such monomers, the particles are of relatively large diameter. The cross-linking agent is sometimes sparingly water soluble. Hydrophobic characteristics can also be provided with monomers such as lower alkyl acrylates suitably methyl methacrylate or ethyl methacrylate or a vinyl pyridine.

Vinyl pyridines suitable for use in the invention are 2-vinyl pyridine, 4-vinyl pyridine and 2-methyl-5-vinyl pyridine.

The metal or metal compound particles are preferably fine evenly sized materials having a uniform diameter smaller than the resultant microsphere diameter, typically below 1000 Å. The metals are preferably the electron dense heavy metals having a high atomic number above 50, preferably above 75 such as Pb, Co, Pt, Au, Fe. The metal may be magnetically attractable such as Fe, Ni, Co or alloys thereof or an inorganic magnetic compound such as a metal oxide. The magnetic material is preferably a magnetic iron oxide of the formula $Fe_3O_4$. Some hard, ceramic type ferrites, such as lithium ferrites can also be used. The ratio of metal to total monomers is usually from 1 to 20% by weight. The amount of metal in the final microsphere product after separation of the non-metal containing microspheres is generally from 1 to 50% by weight.

The microsphere suspension is pH sensitive and in order to avoid agglomeration, the microsphere suspension is adjusted to a pH of about 7 by adding an alkali metal hydroxide such as NaOH to the system, or acid whatever the case may be.

EXAMPLE 1

| Monomer | Wt., g | % |
|---|---|---|
| Methyl methacrylate | 1.59 | 53 |
| Ethylene glycol dimethacrylate | 0.21 | 7 |
| 2-Hydroxyethyl methacrylate | 0.90 | 30 |
| Methacrylic Acid | 0.30 | 10 |

The monomer mixture is added to one gram of an aqueous magnetic iron suspension (from Ferrofluidics Cat. No. A01, 20 gauss/ml, 5% iron wt/vol.) and then diluted with one gram of Triton X405 surfactant.

The resultant mixture was de-aerated with argon gas and subjected to 0.2 megarad of cobalt gamma irradiation at 0° C. The resultant reaction product was then adjusted to pH 7 with NaOH followed with purification of microspheres.

EXAMPLE 2

When Example 1 was repeated without the magnetic particles the rate of polymerization decreased. The redox activity of the particles is further indicated since the rate of polymerization is temperature dependent.

EXAMPLE 3

The composition was as follows:

| Monomer | Wt., g. | % |
|---|---|---|
| 2-hydroxyethylmethacrylate | 1.8 | 60 |
| bis-acrylamide | 0.3 | 10 |
| Acrylamide | 0.6 | 20 |
| Methacrylic acid | 0.3 | 10 |
| Aqueous magnetic iron suspension (5% iron oxide) | 1.0 | | adjusted to 100 cc of 0.4% polyethylene oxide (M.W. 20,000) irradiated at 20° C. for one hour with cobalt 60 gamma (0.4 mr). The particles containing 2% iron by weight had an average diameter of approximately 0.5 microns.

EXAMPLE 4

The following reagents were introduced into a container;

| Methacrylic acid | 0.1 g |
|---|---|
| 2-hydroxyethyl methacrylate | 0.3 g |
| Acrylamide | 0.3 g |
| bis-acrylamide | 0.3 g |
| Aqueous magnetic iron oxide suspension (5% iron oxide) | 0.2 g |
| allyl amine | 0.001 g |
| Fluorescein isothiocyanate (FITC) | 0.005 g |

The mixture was made up to a volume of 50 ml by adding distilled water containing 0.4% to polyethylene oxide (M.W. 200,000). After degassing with nitrogen it was irradiated in the Co γ source (radiation dose: 1 megarad). Iron containing fluorescent polymeric particles were formed during irradiation. The reaction product was passed through a column of Sepharose 2B and then through a mixed-bed ion exchange resin (Biorad No. RG 501-X8).

Further purification was achieved by introducing a bar magnet into the aqueous suspension of magnetic microspheres. The supernatant liquid was removed by means of a pipette and the particles attracted by the poles of the magnet were resuspended in distilled water. This operation was repeated twice. The diameter of magnetic highly fluorescent microspheres obtained varied between 1500 to 2500 Å.

Several polymerizations were carried out according to the procedure of Example 4 but in presence of increasing amounts of sodium dodecyl sulfate (SDS).

The table below shows the effect of SDS concentration on the diameter of fluorescent magnetic microspheres.

| Example | SDS, g | Av. Diam. Å |
|---|---|---|
| 4 | 0 | 2000 |
| 5 | 0.01 | 1500 |
| 6 | 0.02 | 1200 |
| 7 | 0.03 | <1000 |
| 8 | 0.04 | <1000 |

EXAMPLE 9

The following mixture was made up:

| 2-amino ethylmethacrylate hydrochloride | 0.05 g |
|---|---|
| 4-vinyl pyridine | 0.175 g |
| bis-acrylamide | 0.025 g |
| Aqueous magnetic iron suspension | 0.1 g |

0.2% polyethylene oxide (M.W. 200,000) solution was added to the above mixture to a total volume of 25 ml, which was degassed as in previous examples and irradiated in the Co γ source (radiation dose 1 megarad) after purification through Sepharose 2B and ion exchange resin (Biorad No. RG 501-X8) the average diameter of the magnetic particles was 1500 Å.

Several monomer compositions were polymerized by means of a redox initiator system.

The following table gives the compositions of the mixtures which yielded magnetic microspheres.

| Example | Monomer mixture | Monomer concentration | SDS | Aqueous iron oxide | NaHSO$_3$ | FeSO$_4$ (NH$_4$)$_2$SO$_4$ . 6H$_2$O | K$_2$S$_2$O$_8$ |
|---|---|---|---|---|---|---|---|
| | | | | g/100 g of H$_2$O | | | |
| 10 | I* | 3.2 | 0.1 | 2 | 0.04 | 0.0024 | 0.08 |
| 11 | I | 3.2 | 0.1 | 2 | 0.04 | — | 0.08 |
| 12 | II** | 3.36 | 0.1 | 2 | 0.04 | — | 0.08 |
| 13 | I | 3.5 | 0.1 | 2 | 0.04 | — | 0.08 |

| *Composition of mixture I; | |
|---|---|
| MAA | 20% |
| HEMA | 20% |
| EGDMA | 7% |
| MMA | 53% |
| **Composition of mixture II; | |
| MAA | 19% |
| HEMA | 19% |
| EGDMA | 7% |
| MMA 53% | |
| 6 amino hexyl methacrylate hydrochloride | 5% |

The reactions were carried out using 50 g batches (examples 10,11,12 and 13) at room temperature for 145 minutes in a nitrogen atmosphere.

In all cases magnetic microspheres were produced. The diameters of particles of examples 11 and 12 were 700 Å and 1500 Å respectively.

EXAMPLE 14

The copolymer methacrylate microspheres containing iron were covalently coupled to fluorescent dyes, radioactive molecules, and proteins (plant lectins and antibodies). These reagents were used to label cell surface receptors and antigens and (1) map the distribution of specific molecular components on cell surfaces by light and electron microscopy, (2) in agglutination assays and (3) for the separation of specific cell types by the use of magnetic fields.

I. Purification of Microspheres

The iron-microsphere suspension of Example 1 was purified on a mixed-bed ion exchange column and centrifuged at 30,000 g for 45 min. at 4° C. on a discontinuous gradient consisting of 20% (w/w) sucrose upper layer and 60% (w/w) lower layer. Three fractions brown in color were recovered: (1) an upper band in the 20% sucrose fraction; (2) a lower band in the 60% sucrose layer and a pellet. The average size of the particles from the upper and lower fractions was 35-40 nm as measured by SEM. Iron analysis of these fractions are as follows.

|        | % Fe |
|--------|------|
| Pellet | 42.4 |
| Lower  | 28.4 |
| Upper  | 6.2  |

The upper and lower fractions were used in cell surface labeling studies.

II. Preparation of Reagents for Cell Surface Labeling

The Fe-microspheres were tagged with the fluorescent dye, fluorescein isothiocyanate as follows:

Fe-microspheres were derivatized with diaminoheptane by activation of the HEMA hydroxyl groups with cyanogen bromide. Fifty ml of Fe microspheres (1 mg/ml) were reacted at pH 10.5 with 1 gm of CNBr at 25° C. for 20 min. Diaminoheptane was coupled to the CNBr activated microspheres by stirring the suspension of microspheres at 4° C. in the presence of 0.01 M diaminoheptane at pH 9.5 overnight. Subsequently, excess diaminoheptane was removed by dialysis against 0.05 M sodium carbonate pH 9.5.

Fluorescein isothiocyanate was added to the suspension of diaminoheptane-derivatized microspheres at a final concentration of 2 mg/ml. The reaction was carried out in 0.01 M carbonate buffer at pH 9.5 and 25° C. for 12 hours. Uncoupled fluorescein dye was removed by extensive dialysis against 0.10 M phosphate buffer.

Lectins (concanavalin A, ricin, or wheat germ agglutinin) and antibodies (goat antirabbit immunoglobulin) were coupled to the fluorescent-Fe microspheres as follows:

The Fl-Fe microspheres were rederivatized with diaminoheptane by the carbodiimide procedure. 25 mg of 1 ethyl-3(-3-dimethylaminopropyl) carbodiimide was added to 5 ml of Fl-Fe microsphere in 0.01 M diaminoheptane at 4° C. and pH 7.0.

After 3 hours of stirring, excess diaminoheptane was removed by extensive dialysis against 0.01 M phosphate buffer pH 7.0. The diaminoheptane derivatized microspheres were activated with 1.25% glutaraldehyde at 25° C. for 1 hour. After the excess glutaraldehyde was removed by dialysis overnight at 4° C., the plant lectins, ConA, ricin or wheat germ agglutinin, or alternatively, goat antirabbit Ig antibody was added to the microsphere suspension at a concentration of 0.5-1.0 mg/ml. The coupling reaction was carried out at 25° C. overnight.

Unbound protein was separated from the protein-microsphere conjugates by either centrifugation on a sucrose gradient as previously described or column chromatography on Sepharose 6B. III. Activity and Specificity of the Microsphere Reagents.

The binding activity and specificity of the lectin or antibody Fe-microsphere reagents was tested in a variety of procedures.

A. Agglutination Assay

Fe-microspheres bonded to ricin or wheat germ agglutinin were shown to agglutinate human red blood cells. Agglutination was prevented when specific lectin inhibitors, i.e., galactose for ricin or N-acetylchitobiose for WGA, was added to the agglutination assay.

B. Binding to Sephadex or Sepharose Beads

WGA-Fluorescein-Fe microspheres were shown to bind to Sepharose beads which had been previously coupled to ovomucoid, a glycoprotein exhibiting binding sites for WGA. The microspheres did not bind to uncoupled Sepharose as observed by fluorescent microscopy. Ricin fluorescent-Fe microsphere reagents were shown by fluorescent microscopy to specifically bind to Sepharose in the absence of the inhibitor D-galactose. No binding was observed in the presence of this inhibitor.

Goat antirabbit immunoglobulin antibody fluorescent Fe-microspheres were shown to bind to Sepharose beads to which rabbit Ig had been coupled. This binding was inhibited when excess free rabbit immunoglobulin was present.

IV. Cell Surface Labeling

Fluorescein-Fe microspheres conjugated to lectins or antibodies were used to label specific receptors and antigens on the surface of a variety of cells. Cell surface labeling was visualized by fluorescent and electron microscopy.

Microspheres bonded to concanavalin A were shown to label sites on Dictyostelium Discoideum cells as observed by SEM. The microspheres were approximately 500 Å (50 nm) in diameter. No binding to the cells was observed in the presence of 0.05 M α-methyl mannoside, an inhibitor of concanavalin A.

WGA-microspheres and ricin microspheres were observed to specifically bind to red blood cells and murine thymocytes and lymphocytes.

The cell mixture in a magnetically permeable enclosure can be subjected to a magnetic field having a significant attraction for multiple bead labeled cells and small attraction for single beads. The labeled cells will accumulate at the wall of the container adjacent the magnet. The remainder of the mixture can be removed from the container.

Recovery of labeled cells can be enhanced and collection of individual beads reduced by utilization of velocity forces to neutralize the magnetic attraction forces of individual beads. For example, the mixture can be flowed through a tube, a portion of which is within a magnetic field. The magnetic field can then be terminated and the cell subpopulation recovered by flowing a wash solution through the tube.

Each cell has a plurality of specific receptor site such as antigen or antibody which can be covalently coupled to the beads. Thus, when the protein labeled magnetic beads are added to a mixed protein or cell population a plurality of beads will specifically bind to the receptor sites on each cell and the remaining beads will remain in suspension. The bead labeled all subpopulation can be separated from the suspended beads and non-labeled cells due to the higher magnetic susceptibility of the multiple-bead-cell combination.

The magnetic cell sorter can also be utilized to purify the beads by removing non-magnetic beads. After bead purification, the cell binding can be conducted within the instrument before initiation of the cell separation and purification cycle.

Referring now to FIG. 1 a static mode magnetic cell separator 10 includes a magnetically permeable container 12 for receiving a suspension 13 containing cells 14 having magnetic beads 16 attached through an antigen-antibody couple to the membrane of the cell. A source of magnetic field 18 such as a bar magnet, horseshoe magnet or electromagnet is placed adjacent to a wall portion of the container. The cells 14 will accumulate at 24 adjacent the poles 20,22 which generate the highest flux density. The non-tagged cell and protein ingredients remain in the suspension 13 and can be removed by decantation or drained through outlet 26 when valve 28 is open. The magnetic field is then terminated and the tagged cell subpopulation collected. The beads may also contain bound fluorescent dye molecules.

Figure 2:
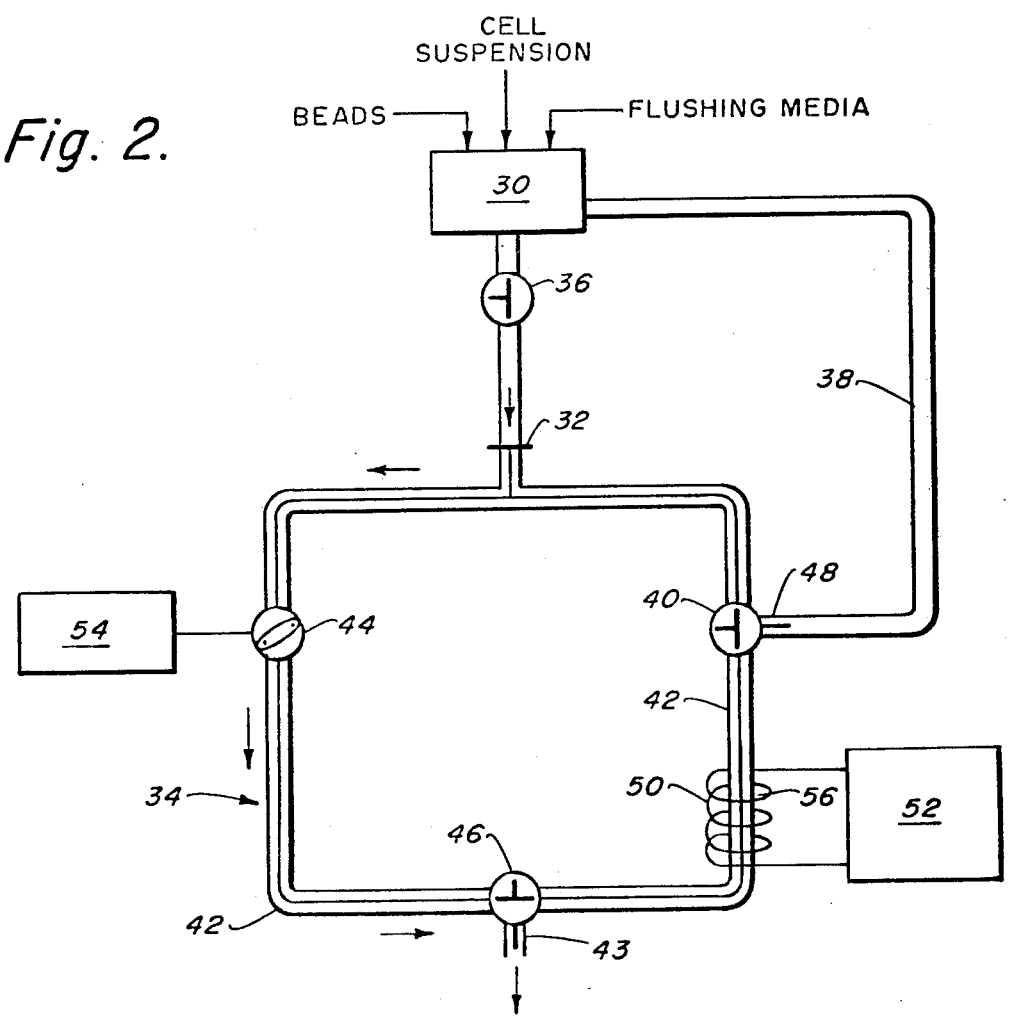
FIG. 2 is a schematic view of a dynamic-mode magnetic cell separator.

A more complete system is illustrated in FIG. 2. The system includes a mixing chamber 30 connected to the inlet 32 of a cell sorter circuit 34 by a valve 36 and to recycle line 38 by three way valve 40. The sorter circuit includes a length of tubing 42, preferably of capillary size, having a pump 44, suitably a peristaltic pump, an outlet 43 connected to valve 46 and a recycle junction 48 connected to valve 40. A magnet, such as an electromagnetic coil 50 surrounds a portion of the tubing 42 and is connected to variable power supply 52.

The cell sorter can also be utilized to purify the magnetic beads. An analysis started by adding a bead suspension to container 30 with valve 36 turned toward inlet 32, valve 46 toward line 42 and valve 40 toward line 42. Valve 36 is then closed and controller 52 turned on to energize coil 50 and controller 54 turned on to start pump 44. The bead suspension will circulate through circuit 34 until all magnetic beads accumulate along the wall portion 56 of the tubing within the magnetic field. Valve 46 is then turned toward outlet 43 to remove the suspension media containing the non-magnetic beads.

Valve 46 is again turned toward line 42, valve 36 toward inlet and valve 40 toward recycle line 38. Flushing media is added to container 30 and after introduction into circuit 34 valve 36 is closed. Controller 52 is turned off and the flushing media will suspend the beads and return them to container 30.

The magnetic beads may be derivatized before purification or at this stage, specific antigen on antibody is attached to the beads by appropriate covalent reactions with the functional groups. A cell suspension is added to container 30, valve 36 opened until the cell-bead suspension is injected into circuit 34 and valve 36 then closed. Valves 40 and 46 are turned toward line 42 and the suspension circulated by pump 44 with magnet 50 operating until all the cells containing multiple beads accumulate along the wall portion 56. The speed of flow is adjusted such a that for the field applied at 56 only the magnetically labeled cells are attracted and immobilized by the field. The attraction force on the magnetic microspheres is not sufficient to overcome the linear force applied by the pump. Valve 46 is then turned toward outlet 43 and the suspension containing non-labeled cells and individual beads collected. The labeled cells are then flushed and collected in container 30 as discussed above.

The efficiency and ease of cell separation can be enhanced by use of a high gradient magnetic separator (HGMS). HGMS represents a technological breakthrough in the efficient separation of very weakly magnetic particles for which conventional magnetic separators are ineffective. Various applications of this technique are now in progress, at the industrial level, in the fields of mineral processing and water pollution control. The magnetic force Fm on the particle to be separated is $$Fm \sim X \, Ho \, dHO/dx$$

where X is the magnetic susceptibility, Ho is the applied field, and dHO/dx is the field gradient.

Both X and dHO/dx can be improved. Magnetite provides a large effective particle of high XHo. The second and more important problem of increasing the magnetic field gradient, dHO/dx, is solved by passing the magnetically labeled cells down a vertical tube filled with a filamentary ferromagnetic matrix (e.g., siliconized steel wool), which has a solid volume of ~5% of the tube volume. This ferromagnetic matrix is capable of generating very intense field gradients ($\sim 1kG/\mu$). The utilization of the ferromagnetic matrix is the heart of the HGMS technique and allows the magnetic force to be increased, via the gradient, far more substantially than can be accomplished by just magnetic seeding. By varying the diameter of the ferromagnetic filaments to match the diameter of the microspheres, the magnetic force can also be optimized. This technique will permit the use of electromagnets the Ho of which is considerably lower than that of permanent magnets.

Figure 3:
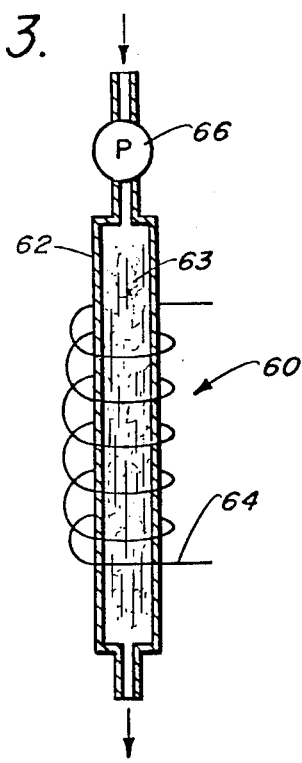
FIG. 3 is a schematic view of a high gradient magnetic cell separator.

Referring now to FIG. 3, the HGMS 60 includes a tube 62 containing filamentary ferromagnetic matrix 63 and surrounded by an electromagnetic coil 64. As pump 66 pumps the bead labeled cells down the tube the labeled cells will be attracted to and attach to the filaments 63. The cell subpopulation can then be flushed and collected.

V. Cell Separation Using Magnets

The attraction of cells labeled with Fe-microspheres to a magnet was initially tested on red blood cells (RBC). As shown in FIG. 1, cells sensitized with rabbit anti-RBC antibodies, and subsequently, labeled with Fe microspheres conjugated to goat anti-rabbit immunoglobulin (Ig) antibodies were quantitatively retained by a horseshoe magnet (12 lb. pull) placed against the side of the pipet; unsensitized cells treated with the Fe-microsphere conjugates sedimented past the magnet to the bottom of the pipet.

Magnetic cell separation was tested in two independent systems. In the first, glutaraldehyde-fixed mouse thymocytes indirectly labeled for surface antigens with fluorescein-Fe microsphere-antibody conjugates were mixed in varying proportions with unlabeled human RBC's. The mixture was layered over PBS containing 5% bovine serum albumin and placed in a magnetic field. After 2 hours the solution was eluted to separate cells attracted to the magnet from those that were not. Differences in cell morphology and fluorescent labeling were used to analyze the cell fractions. As indicated in Table I, over 99% of the labeled thymocytes were attracted by the magnet.

second passage of dissociated cells through the magnetic field.

Application of these fluorescent-Fe-microspheres as

Table I

| | Magnetic Cell Separation | | | | | | |
|---|---|---|---|---|---|---|---|
| | Before Separation | | | | After Separation | | |
| Experiment | No. of Cells Counted Total | Labeled (F1)[a] | Percent Labeled (F1) | Magnet | No. of Cells Counted Total | Labeled (F1)[a] | Percent Labeled (F1) |
| 1. RBC/Thym. | 521 | 429 | 82.3 | Attracted | 509 | 499 | 98.0 |
| | | | | Not Attracted | 500 | 2 | 0.4 |
| 2. RBC/Thym. | 580 | 179 | 30.9 | Attracted | 532 | 487 | 91.5 |
| | | | | Not Attracted | 520 | 1 | 0.2 |
| 3. Lymphocytes | 252 | 92 | 36.5 | Attracted | 206 | 168 | 81.6 |
| | | | | Not Attracted | 211 | 3 | 1.4 |
| 4. Lymphocytes | 210 | 82 | 39.1 | Attracted | 144 | 110 | 76.4 |
| | | | | Not Attracted | 303 | 9 | 3.0 |

[a]Labeled with fluorescein-Fe-microspheres-antibody conjugates

In red blood cell-thymocyte experiment 1, $2.1 \times 10^6$ glutaraldehyde-fixed RBC were mixed with $8.2 \times 10^6$ fixed mouse thymocytes labeled sequentially with rabbit anti-thymocyte antiserum followed by fluorescein-Fe-microsphere-goat anti-rabbit immunoglobulin conjugates. Experiment 2 was carried out under similar conditions, except that $8.1 \times 10^6$ RBC were mixed with $3.3 \times 10^6$ thymocytes. The number of fluorescent cells was measured. Approximately, $5 \times 10^6$ mixed cells were layered on a 5% BSA-PBS solution. A magnet (12 lb. pull) was placed against the wall of a 0.9 cm diameter column at the interface. After 2 hours at 4° C. the column was gently eluted with PBS to separate cells attracted to the magnet from those which were not. The magnet was then removed from the side of the column and the cells pulled to the side of the column were displaced by shaking the column. The two cell fractions were analyzed for fluorescent (F1) labeling and the cell type using a Leitz Dialux fluorescent microscope.

In experiments 3 and 4, $1 \times 10^6$ mouse spleen lymphocytes purified by the Ficoll-isopaque method (20) were directly labeled with 0.1 ml of fluorescein-Fe microsphere-goat antimouse Ig conjugates at 4° C. Cells were washed and the percentage of cells with fluorescein label was measured. Approximately, $5 \times 10^5$ cells were then layered on a Ficoll-isopaque layer and subjected to magnetic separation as described above.

In a more applicable system, this magnetic cell separation technique was used to separate out lymphocytes with Ig receptors (B-cells) from a mixed population of spleen lymphocytes. Fluorescein Fe-microspheres coupled to goat anti-mouse Ig were used to directly label unfixed lymphocytes. Labeled cells could be distinguished from unlabeled cells under fluorescent microscope. In agreement with literature values approximately 37% of the cells were labeled (Table I). After subjecting the mixture to a magnetic field (12 lb. pull horseshoe magnet) for 2 hours at 4° C., 97–99% of the labeled cells (principally B-lymphocytes) were attracted by the magnet, leaving a highly purified population of unlabeled lymphocytes (T-cells). Some unlabeled cells, however, were also in the cell population which was retained by the magnet. This resulted largely from nonspecific aggregation of the lymphocytes and nonspecific adhesion of cells to the glass wall of the pipet. Further removal of unlabeled cells from the predominantly labeled population could be achieved by a visual markers for SEM was also demonstrated by the labeling of wheat germ agglutinin receptors on cultured Hela cells. Specificity was verified by the absence of binding of the WGA-microsphere conjugate in the presence of N-acetyl-chitobiose, an inhibitor of WGA.

Copolymer microspheres containing iron particles and synthesized by emulsion polymerization in the presence of SDS were also used in cell labeling and cell separation studies. The microspheres were approximately 750 Å in diameter and exhibited similar surface properties as copolymer microspheres without iron.

The iron-copolymer microspheres were tagged with fluorescein isothiocyanate using the CNBr method. Goat anti-mouse Immunoglobulin was then coupled to diaminoheptane-derivatized spheres using the two step glutaraldehyde reaction.

The reagent were used to label lymphocyte cells containing immunoglobulin on the surface. Results using fluorescent and scanning electron microscopy indicated that 35% of mouse spleen lymphocytes were labeled. When this mixture of labeled and unlabeled cells was passed through a magnetic field over 90% of the labeled cells were attracted to the magnet.

These new cell surface reagents have potential applications in biochemical and microscopic studies of specific components on cell surface membranes. The magnetic properties of these spheres can be utilized to isolate specific types of cells. The magnetic cell sorting technique described here is quite simple, but more sophisticated instrumentation can be envisioned to continuously separate cells which differ in the number, as well as the nature of surface molecules. Such techniques would be particularly useful for processing large numbers of cells for biochemical and immunological studies. Magnetic properties can also be used in the separation of labeled cell surface membranes from intracellular membranes, as well as in the purification of specific membrane-bound receptors which have been solubilized in mild detergents. Stronger magnetic fields may be useful in such applications. Alternatively, the dense properties of these spheres can be exploited to separate membranes and receptors by density or velocity purturbation techniques using ultracentrifugation.

The iron content of these microspheres also permits their use as visual markers for transmission electron microscopy (TEM). This enables one to correlate labeling information derived from light and SEM with cellular ultrastructure obtained by TEM. Their size, iron content, and surface properties can be varied for multiple labeling, and complements the use of ferritin as a visual marker. The advantage of using gold granules as markers for SEM has already been demonstrated. In principle, similar reactions used in the synthesis of these iron containing polymeric spheres can be adapted for preparing microspheres containing gold or other heavy metals.

Finally, these or related reagents may have future clinical applications. Magnetic microspheres carrying cytotoxic drugs, enzymes or radioisotopes could, in principle, be localized in a certain tissue of a body such as a tumor, by applying powerful magnets and serve as diagnostic or therapeutic agents.

These results demonstrate the feasibility of using these new microsphere reagents (1) to map the distribution of specific sites on cell surfaces by light and electron microscopy; and (2) to separate specific populations of cells with magnetic fields.

Such reagents should also be valuable (1) in biochemical and immunochemical binding and agglutination assays, (2) in the separation of cells, membranes and specific receptors by magnetic or density techniques and (3) as probes for in vitro cellular studies.

It is to be realized that only preferred embodiments of the invention have been described and that numerous substitutions, modifications and alterations are permissible without departing from the spirit and scope of the invention as defined in the following claims.

What is claimed is:

1. An apparatus for separating a biological cell subpopulation from a biological cell mixture including magnetic functional polymeric particles bound to the cells of said subpopulation comprising in combination:

tubular means defining a circuit having an inlet a first and second outlet and a wall portion permeable to a magnetic field disposed in said circuit;

first two-way valve means mounted in said circuit and connected to said first outlet;

second two-way valve means mounted in said circuit and connected to said second outlet;

magnetic field means mounted to generate a magnetic field adjacent said wall portion;

a mixing chamber having a particle inlet, a cell suspension inlet, flushing media inlet, recycle inlet and an outlet connected by means of a third valve to the inlet to the circuit;

pump means for pumping particle or cell suspension through said circuit; and a recycle conduit connected to said second outlet to the recycle inlet.

2. An apparatus according to claim 1 in which the field means includes an electromagnet and further including variable power means for applying a selected current to the electromagnet and switching means connected to the power means.

3. An apparatus according to claim 2 in which the field means further includes means for generating a high field gradient in the vicinity of the wall portion.

4. An apparatus accoridng to claim 3 in which the high gradient field means includes filamentary magnetizable material disposed within said tubular means adjacent said wall portion.

5. An apparatus according to claim 1 in which the pump means is disposed within said circuit.

6. An apparatus according to claim 5 in which the pump means is a peristaltic pump.

7. An apparatus according to claim 1 in which the tubing is of capillary size.

8. An apparatus according to claim 1 in which the magnetic field means is disposed between said first and second outlets.

* * * * *